United States Patent [19]

Finke et al.

[11] 4,203,914
[45] May 20, 1980

[54] SILYL ESTERS OF PERFLUOROALKANESULPHONIC ACID ESTERS AND A PROCESS FOR THEIR PREPARATION

[75] Inventors: Ulrich Finke, Ettlingen; Hans-Heinrich Moretto, Cologne; Hans Niederprüm, Monheim; Helmut Vorbrüggen, Berlin, all of Fed. Rep. of Germany

[73] Assignee: Bayer Aktiengesellschaft, Leverkusen, Fed. Rep. of Germany

[21] Appl. No.: 2,112

[22] Filed: Jan. 8, 1979

[30] Foreign Application Priority Data

Jan. 25, 1978 [DE] Fed. Rep. of Germany ....... 2803125

[51] Int. Cl.² ............................................. C07F 7/08
[52] U.S. Cl. ................................................... 556/428
[58] Field of Search ................................. 260/448.2 N

[56] References Cited

U.S. PATENT DOCUMENTS

| | | | |
|---|---|---|---|
| 3,949,136 | 4/1976 | Deiner et al. | 260/448.2 N X |
| 3,997,580 | 12/1976 | Morehouse | 260/448.2 N |

*Primary Examiner*—Paul F. Shaver

*Attorney, Agent, or Firm*—Sprung, Felfe, Horn, Lynch & Kramer

[57] ABSTRACT

A process for the preparation of a perfluoroalkanesulphonic acid ester of the formula $$C_nF_{2n+1}SO_3Si\ R^1R^2R^3$$

comprising reacting a silane of the formula $$R^1R^2R^3R^4Si$$

with a perfluoroalkanesulphonic acid of the formula $$C_nF_{2n+1}SO_3H$$

wherein
  $R^1$, $R^2$ and $R^3$ each independently is alkyl with 1 to 6 carbon atoms,
  $R^4$ is methyl, and
  n is from 1 to 12.

Compounds wherein the total number of carbon atoms in Cn, $R^1$, $R^2$ and $R^3$ is at least 6 are new and especially useful as silylating agents in organic cyntheses.

4 Claims, No Drawings

SILYL ESTERS OF PERFLUOROALKANESULPHONIC ACID ESTERS AND A PROCESS FOR THEIR PREPARATION

The present invention relates to new silyl esters of perfluoroalkanesulphonic acids, of the general formula $$C_nF_{2n+1}SO_3SiR^1R^2R^3 \quad (I)$$

wherein
$R^1$, $R^2$ and $R^3$ are identical or different and represent a straight-chain or branched, lower alkyl radical with 1-6 C atoms,
n denotes an integer from 1-12 and the total number of carbon atoms in Cn, $R^1$, $R^2$ and $R^3$ is at least 6 and preferably at least 8.

The present invention also relates to a process for the preparation of the compounds I.

Of the trialkylsilyl esters of perfluoroalkanesulphonic acid, only the trimethylsilyl esters of trifluoromethanesulphonic acid and of pentafluoroethanesulphonic acid have hitherto been known (compare, for example, Chem. Ber. 103, page 868 (1970). Trimethylsilyl trifluoromethanesulphonate—also called "triflate" for short—is a valuable silylating agent and is also used as a catalyst in syntheses of nucleosides (compare, for example, Synthesis 4, 259 (1976) and DT-OS (German Published Specification) 2,508,312).

"Triflate" was hitherto prepared, for example, by reacting silver trifluoromethanesulphonate or mercury trifluoromethanesulphonate with trimethylchlorosilane (Chem. Ber. loc. cit.) or by reacting trifluoromethanesulphonic acid with trimethylchlorosilane (for example Naturforschung B 27, 4448 (1972). The disadvantage of these processes is that they are relatively expensive or give unsatisfactory yields.

In addition to relating to a number of new silyl esters of perfluoroalkanesulphonic acids, the present invention also relates to a process for the preparation of silyl esters of perfluoroalkanesulphonic acids, of the general formula $$C_nF_{2n+1}SO_3SiR^1R^2R^3$$

wherein
$R^1$, $R^2$ and $R^3$ are identical or different and represent a lower alkyl radical with 1-6 C atoms and
n denotes an integer from 1-12, which is characterized in that a silane of the general formula $$R^1R^2R^3R^4Si$$

wherein
$R^1$, $R^2$ and $R^3$ have the meaning given and
$R^4$ represents methyl, is reacted with a perfluoroalkanesulphonic acid of the general formula $$C_nF_{2n+1}SO_3H \quad (n=1-12)$$

It has been found, surprisingly, that perfluoroalkanesulphonic acids with methyl-alkylsilanes give the desired esters in almost quantitative yield. This is surprising, above all, since in the literature the view was hitherto always taken that tetramethylsilane, for example, cannot be reacted with trifluoromethanesulphonic acid (compare, for example, Chem. Ber. loc. cit. or Chem. Reviews 1977, volume 77, No. 1 page 69-92).

The advantage of the process according to the invention is also that even the higher esters can be made available in good yield.

Compared with the substances already known, the advantage of the compounds according to the invention is that an increased silylating action is obtained with increasing number of C atoms, especially from 5 C atoms, in the perfluoroalkyl radical. Silyl esters of perfluoroalkanesulphonic acid in which $R^1$ and $R^2$=methyl and $R^3$=$C_nH_{2n+1}$ (n=2-6) are powerful silylating reagents which lead to silyl ethers or esters with, for example, increased stability to hydrolysis (in comparison with the silyl ethers and esters hitherto available using the known trimethylsilyl-"flates"). Methylalkylsilanes, such as, for example, tetramethylsilane (TMS), butyltrimethylsilane, dibutyldimethylsilane, pentylbutyldimethylsilane, isopentylbutyldimethylsilane, ethyltrimethylsilane and tripropylmethylsilane, are used as the starting material for the process according to the invention.

Silanes of this type are available, for example, via direct synthesis (by the so-called Müller-Rochow process), via organometallic synthesis (for example a Grignard reaction) or via hydrosilylation processes.

Perfluoroalkanesulphonic acids are industrial products and are available via the electrofluorination of alkanesulphonyl fluorides and subsequent reaction of the products with aqueous alkali and $H_2SO_4$. Examples of perfluoroalkanesulphonic acids are, for example, $CF_3SO_3H$, $C_4F_9SO_3H$ and $C_8F_{17}SO_3H$.

The process according to the invention can be carried out either with or without solvents. In general, all solvents which do not undergo a reaction with the sulphonic acid itself, such as, for example, pentane, hexane, cyclohexane, pertroleum ether or benzene, can be used.

The temperature at which the process according to the invention is carried out is preferably below the boiling point of the tetraalkylsilane, in particular from about $-30°$ C. to $+60°$ C.

The process according to the invention is preferably carried out under pressure of the surrounding atmosphere, because this requires the least effort. However, if desired, higher or lower pressures can also be used.

The conversions achieved in the process according to the invention are in general 90–100%, in each case relative to the reactant employed in the lowest amount. As a rule, the tetraalkylsilane is employed in excess (up to about 20%) and, after the reaction has ended, excess silane is stripped off; because of the purity obtained, distillation of the product is superfluous in most cases. Unreacted tetraalkylsilane can be re-used in the process according to the invention.

The process according to the invention will now be illustrated in still further detail with the aid of the examples which follow.

EXAMPLE 1

1.15 mols of tetramethylsilane were added dropwise to 1 mol of $CF_3SO_3H$ in a 1 liter three-necked flask with a reflux condenser, internal thermometer and dropping funnel at 0° C., while stirring. The reaction temperature was kept at 10° C. After the evolution of methane had ended, the excess tetramethylsilane was stripped off. According to 19 F- and 1H-NMR spectroscopy, the reaction product was the pure trimethylsilyl ester of trifluoromethanesulphonic acid (boiling point 140° (750 mm Hg).

EXAMPLE 2

The reaction of $C_4F_9SO_3H$ with tetramethylsilane was carried out analogously to Example 1.

Yield=92% of $C_4F_9SO_3Si(CH_3)_3$, boiling point 70° C./10 mm Hg, 1,H-NMR: $Si(CH_3)_3$; 29 Hz singlet.

EXAMPLE 3

The reaction of $C_8F_{17}SO_3H$ (solid) with tetramethylsilane was carried out at 15°–20° C., and otherwise analogously to Example 1.

Yield=90% of $C_8F_{17}SO_3Si(CH_3)_3$, boiling point 70°–90° C./1.1 mm Hg, 1H-NMR: $Si(CH_3)_3$-singlet 29 Hz.

EXAMPLE 4

The reaction of trimethylbutylsilane with $C_4F_9SO_3H$ was carried out at 20° C. The reaction product was identified, by NMR sprectroscopy, as $(CH_3)_2(C_4H_9)Si-OSO_2C_4F_9$. Yield>90%, 1H-NMR: $Si(CH_3)_2$-singlet 27.5 Hz; $SiC_4H_9$-multiplet 37–96 Hz.

EXAMPLE 5

Reaction of $C_4F_9SO_3H$ with $(CH_3)_2(C_4H_9)_2Si$, identification of the product analogously to Example 4: $CH_3(C_4H_9)_2SiOSO_2C_4F_9$.

Yield: 90%, 1H-NMR: $SiCH_3$ 27.5 Hz singlet; $Si(C_4H_9)_2$ multiplet from 40–125 Hz.

EXAMPLE 6

$C_4F_9SO_3H + (CH_3)_2(C_4H_9)Si(C_5H_{11})$; identification of the product analogously to Example 4: $me(C_4H_9)(C_5H_{11})SiOSO_2C_4F_9$. Yield: 90%, 1H-NMR: $SiCH_3$ singlet 27.5; $SiC_4H_9$ and $SiC_5H_{11}$ multiplet from 40–120.

EXAMPLE 7

$C_4F_9SO_3H + (CH_3)_3Si(C_5H_{11})$; identification of the product analogously to Example 4: $(CH_3)_2(C_5H_{11})Si-OSO_2C_4F_9$. Yield: 91%, 1H-NMR: $Sime_2$ 27.5 Hz singlet; $SiC_5H_{11}$ 52–145 Hz multiplet.

1H-NMR instrument: 60 MHz; TMS=0 Hz

It will be appreciated that the instant specification and examples are set forth by way of illustration and not limitation, and that various modifications and changes may be made without departing from the spirit and scope of the present invention.

What is claimed is:

1. A process for the preparation of a perfluoroalkanesulphonic acid ester of the formula $$C_nF_{2n+1}SO_3SiR^1R^2R^3$$

comprising reacting a silane of the formula $$R^1R^2R^3R^4Si$$

with a perfluoroalkanesulphonic acid of the formula $$C_nF_{2n+1}SO_3H$$

wherein
$R^1$, $R^2$ and $R^3$ each independently is alkyl with 1 to 6 carbon atoms,
$R^4$ is methyl, and
n is from 1 to 12.

2. A process according to claim 1, wherein the silane is etramethylsilane.

3. A perfluoroalkanesulphonic acid trialkylsilyl ester of the formula $$C_nF_{2n+1}SO_3SiR^1R^2R^3$$

wherein
$R^1$, $R^2$, and $R^3$ have the abovementioned meaning and each independently is alkyl with 1 to 6 carbon atoms,
n is from 1 to 12, and
the total number of carbon atoms in Cn, $R^1$, $R^2$ and $R^3$ is at least 6.

4. A perfluoroalkanesulphonic acid trialkylsilyl ester according to claim 3, wherein n is 5, 6, 7, or 8.

* * * * *